US005199427A

United States Patent [19]
Strickland

[11] Patent Number: 5,199,427
[45] Date of Patent: Apr. 6, 1993

[54] MULTI-LAYERED TRANSTRACHEAL CAATHETER

[75] Inventor: Richard D. Strickland, Sandy, Utah
[73] Assignee: Ballard Medical Products, Draper, Utah
[21] Appl. No.: 778,513
[22] Filed: Oct. 18, 1991

Related U.S. Application Data

[63] Continuation-in-part of Ser. No. 600,435, Oct. 19, 1990.

[51] Int. Cl.[5] .............................................. A61M 16/00

[52] U.S. Cl. ........................... 128/207.14; 128/200.26

[58] Field of Search ...................... 128/200.26, 207.14, 128/207.15, 207.29

[56] References Cited

U.S. PATENT DOCUMENTS

| | | | |
|---|---|---|---|
| 2,786,469 | 3/1957 | Cohen | 128/351 |
| 2,991,787 | 7/1961 | Shelden et al. | 128/351 |
| 3,039,469 | 6/1962 | Fountain | 128/351 |
| 3,225,767 | 12/1965 | Smith | 128/351 |
| 3,319,622 | 5/1967 | Shiner | 128/2 |
| 3,788,305 | 1/1974 | Schreiber | 128/2 F |
| 3,948,273 | 4/1976 | Sanders | 128/207.15 |
| 4,033,353 | 7/1977 | La Rosa | 128/351 |
| 4,037,605 | 7/1977 | Firth | 128/351 |
| 4,072,146 | 2/1978 | Howes | 128/2.05 D |
| 4,211,741 | 7/1980 | Ostoich | 264/173 |
| 4,235,229 | 11/1980 | Ranford et al. | 128/207.17 |
| 4,239,042 | 12/1980 | Asai | 128/214.4 |
| 4,344,436 | 8/1982 | Kubota | 128/350 R |
| 4,385,635 | 5/1983 | Ruiz | 128/658 |
| 4,416,273 | 11/1983 | Grimes | 128/207.16 |
| 4,434,963 | 3/1984 | Russell | 251/7 |
| 4,525,156 | 6/1985 | Benusa et al. | 604/28 |
| 4,586,691 | 5/1986 | Kozlow | 251/7 |
| 4,596,563 | 6/1986 | Pande | 604/264 |
| 4,622,968 | 11/1986 | Persson | 128/305 |
| 4,627,433 | 12/1986 | Lieberman | 128/207.16 |
| 4,637,389 | 1/1987 | Heyden | 128/207 |
| 4,641,646 | 10/1987 | Schultz et al. | 128/207.14 |
| 4,649,913 | 3/1987 | Watson | 128/207.14 |
| 4,669,463 | 6/1987 | McConnell | 128/207.14 |
| 4,683,879 | 8/1987 | Williams | 128/200.26 |
| 4,716,901 | 1/1988 | Jackson et al. | 128/343 |
| 4,838,255 | 6/1989 | Lambert | 128/202.16 |
| 4,840,623 | 6/1989 | Quackenbush | 604/280 |
| 4,846,191 | 7/1989 | Brockway et al. | 128/748 |
| 4,864,464 | 9/1989 | Gonzalez | 361/311 |
| 4,869,718 | 9/1989 | Brader | 604/164 |
| 4,886,496 | 12/1989 | Conoscenti et al. | 604/96 |
| 4,898,163 | 2/1990 | George | 128/200.26 |
| 4,953,547 | 9/1990 | Poole, Jr. | 128/203.12 |
| 4,981,466 | 1/1991 | Lumbert | 604/19 |
| 4,981,470 | 1/1991 | Bombeck, IV | 128/635 |
| 4,981,477 | 1/1991 | Schon et al. | 604/264 |
| 4,995,384 | 2/1991 | Keeling | 128/207.18 |
| 5,031,613 | 7/1991 | Smith et al. | 128/207.14 |
| 5,054,482 | 10/1991 | Bales | 128/207.14 |
| 5,058,579 | 10/1991 | Terry et al. | 128/207.14 |
| 5,060,645 | 10/1991 | Russell | 128/207.14 |
| 5,060,646 | 10/1991 | Page | 128/207.14 |
| 5,062,420 | 11/1991 | Levine | 128/204.18 |
| 5,067,496 | 11/1991 | Eisele | 128/207.15 |

FOREIGN PATENT DOCUMENTS

WO89/02761 4/1989 PCT Int'l Appl. .

OTHER PUBLICATIONS

"The Micro-Trach: A Seven-Year Experience with Transtracheal Oxygen Therapy," Henry J. Heimlich et al., Chest, vol. 95, No. 5, (May 1989).
"Transtracheal Oxygen Therapy: A Guide for the Respiratory Therapist", Bryan Spofford et al., Respiratory Care, vol. 32, No. 5 (May 1987).

*Primary Examiner*—Edgar S. Burr

*Assistant Examiner*—Aaron J. Lewis

*Attorney, Agent, or Firm*—Workman Nydegger Jensen

[57] ABSTRACT

A multi-layered transtracheal catheter. The transtracheal catheter has a multi-layer or double wall construction formed of two materials. One material is resistant to kinking. The other material is resistant to mucous buildup. Together, they form a catheter that can remain within the trachea for an extended period of time without needing to be removed for cleaning. The distal end of the catheter is deflected from the remainder of the catheter so that when the catheter is inside the trachea and held against the wall of the trachea, the distal end of the catheter is deflected from the wall so that the distal end is not in contact with the wall of the trachea. The result is reduced irritation to the trachea wall, reduced occlusion of the distal end by mucous buildup, and a more directed and efficient spray of material from the catheter into the right and left main skin bronchi of the lungs.

7 Claims, 4 Drawing Sheets

MULTI-LAYERED TRANSTRACHEAL CAATHETER

THE RELATED APPLICATIONS

This application is a continuation in part of pending application Ser. No. 07/600,435, filed Oct. 19, 1990, in the name of Richard D. Strickland and entitled, "Multi-Layered Transtracheal Catheter."

BACKGROUND

1. The Field of the Invention

This invention relates to medical catheters adapted for insertion into the trachea. More particularly, this invention relates to a multi-layered transtracheal catheter.

2. Review of Technical Background

Patients suffering from chronic oxygen-dependent respiratory failure must have an almost constant supply of oxygen. Today, many patients with chronic oxygen-dependent respiratory failure use nasal cannulas for their oxygen therapy. With nasal cannula therapy, patients receive needed oxygen through tubes which are attached to their nasal passages.

However, there are some disadvantages associated with nasal cannula therapy. One is that before the oxygen can reach the lungs, it must first pass through the nasal passages, the back of the mouth, and the vocal chords. By this route, much oxygen escapes from the mouth and the nose and is lost. There are two problems which result from this loss of oxygen. One is that the patient's oxygen saturation level is lower than it otherwise would be if the oxygen had not been lost. This makes it more difficult for the patient to exercise, and exercise is often an important component of recovery for such patients. A second problem is that since much of the oxygen is lost, patients are forced to carry with them larger containers of oxygen. For many, this is not only burdensome, but also immobilizing, particularly in the case of persons who may be seriously physically weakened due to age or illness.

An additional problem with the use of typical nasal cannula devices is discomfort. A constant flow of dry, cold oxygen in the nasal passages causes drying of delicate nasal membranes. This drying can cause the nasal passage tissues to swell and become sore. As a consequence, less oxygen is delivered through the swollen nasal passages making breathing more difficult so that frequently a patient will attempt to breathe through the mouth, which further complicates the matter. This problem is especially acute during the night when oxygen saturation levels are already at their lowest. In addition, because the nasal cannula is attached around the front of the face, pressure sores often appear on the tops of the user's ears. Also, a patient's face can become irritated by the plasticizers in the attachment strap. Because of these side effects of nasal cannula therapy, patients have been very reluctant to continuously wear such nasal cannula devices as prescribed. Thus, the effectiveness of the therapy is reduced.

Devices and methods have been developed which solve many of these problems One such method, called transtracheal oxygen delivery, requires use of a small polytetrafluoroethylene catheter inserted into the trachea through the skin at the base of the neck. On the end of the catheter is attached a luer connector which connects the catheter to an oxygen source. With the use of this device, oxygen is neither lost nor wasted because it is delivered directly to the trachea. Thus, oxygen delivery is more efficient. Patients are more mobile because they are able to carry around smaller containers of oxygen, and because of better oxygen saturation.

This device and method also solve the problem of irritation of the nose and face. Since the oxygen no longer has to pass through the nose, the nasal tissues no longer become dry and irritated. Further, there is no longer any facial attachments to irritate or encumber the face and ears.

A further advantage of the transtracheal oxygen delivery device and method is the fact that it assists the patient in breathing. Breathing requires a certain amount of work. If a patient has chronic obstructive lung disease, the amount of work needed to breathe is increased. This work is reduced by the delivery of oxygen directly to the lungs by the pressure of the oxygen tank. Thus, with transtracheal oxygen delivery a patient is able to work less to get the same volume of oxygen to the lungs.

Although the transtracheal device and method solves many of the problems and disadvantages of nasal cannula therapy, some problems still remain. For example, some catheters devised for transtracheal oxygen delivery have been made of polytetrafluoroethylene.

Polytetrafluoroethylene appeared to be desireable because of its resistance to the mucous found lining the trachea, so that the mucous did not cling to the catheter. Mucous buildup on the transtracheal catheter causes primarily two problems. First, as the mucous begins clinging to and building up on the catheter, a ball may form which ultimately may become large enough to obstruct the trachea. A second, related problem is that even if the mucous does not build up to the point where it obstructs the trachea, at times, the mucous may tend to slide to the end of the catheter and to build up at that point so that it will occasionally entirely close off and clog the end of the catheter opening. In either case, the result is obstructed and encumbered breathing capacity.

The resistance of polytetrafluoroethylene to the build up of mucous enabled polytetrafluoroethylene catheters to remain in the trachea for thirty days at a time without having to be removed for cleaning, or replacement. Unfortunately, however, such polytetrafluoroethylene catheters would often kink within two to three weeks of placement. When a transtracheal catheter is placed in the trachea, it must be able to make an essentially ninety degree bend after the catheter passes through the neck of the patient so as to extend the end of the catheter down toward the lungs. If the catheter is not flexible enough and does not have sufficient circular memory and resiliency, certain kinds of abrupt action such as swallowing, turning the head, coughing and the like will tend to result in such kinking.

To avoid kinking, one solution appeared to be the use of urethane in forming the catheter rather than polytetrafluoroethylene. Urethane is a soft material with good characteristics of resiliency and circular memory that enable the catheter to resist kinking. It is also hypoallergenic. However, urethane is also hydrophilic, and is thus very susceptible to mucous buildup. As noted above, when mucous attaches itself to the catheter, it will typically form a ball and may clog either the opening of the catheter or the trachea. As a result, although urethane catheters resist the tendency to kink, they typically have to be removed twice a day for cleaning.

An additional problem with transtracheal urethane catheter devices is that because of their softness, they tend to move about excessively with rapid inhalation or exhalation, such as experienced with coughing, sneezing, etc. This causes irritation of the trachea, and induces coughing.

Further, when the catheter is positioned within the trachea, the tip of the catheter may drag against the trachea wall, thereby scooping mucous from the wall of the trachea onto the tip of the catheter. When this occurs, the risk of occlusion of the catheter by mucous buildup increases. Irritation to the trachea wall from contact with the tip of the catheter also increases.

Additionally, spray of material from the catheter tip is directed so that a portion is aimed against the posterior wall of the trachea rather than directly into the right and left bronchi of the lungs, thus causing irritation to the posterior wall of the trachea and inefficient use of the material.

BRIEF SUMMARY AND OBJECTS OF THE INVENTION

In view of the present state of the art, it is an object of the present invention to provide a transtracheal catheter of materials which will not only resist kinking, but will also be resistant to mucous buildup and attachment, thus permitting the catheter to remain in the trachea for extended periods of time.

Still another object of the present invention is to provide a transtracheal catheter that is soft and flexible enough to bend in order to be inserted into the trachea, but is not so soft and flexible that it moves excessively when rapid or abrupt inhalation or exhalation is experienced.

A further object of the present invention is to provide a transtracheal catheter which reduces mucous buildup within the catheter during or after insertion of the catheter into the trachea and reduces irritation to and drying of the posterior wall of the trachea.

Yet another object of the present invention is to provide a transtracheal catheter which is configured such that the spray of gas or irrigant exiting the catheter directly enters the right and left bronchi of the catheter rather than being first scattered along the back wall of the trachea, thus reducing irritation to the trachea and inefficient use of the materials.

These and other objects and advantages of the invention will become more fully apparent from the description and claims which follow, or may be learned by the practice of the invention.

In accordance with the foregoing objects, the present invention is directed to a transtracheal catheter having a multi-layer or double wall construction formed of two or more materials. One material is resistant to kinking. A second material is resistant to mucous buildup. Together, they form a catheter that can remain within the trachea for an extended period of time (e.g., typically up to 30 days) without needing to be removed for cleaning.

The catheter of the present invention is formed having a distal end which is bent in an angle away from the remaining portion of the catheter body such that when the catheter is positioned within the trachea against the posterior wall, the tip of the catheter projects away from and does not contact the posterior tracheal wall. Thus, when any upward or downward motion of the catheter occurs, the catheter tip does not drag against the posterior wall scooping mucous into its lumen. This upward and downward motion of the catheter may occur during tracheal movement. Tracheal movement occurs during breathing, swallowing, coughing, or even turning of the head. During this movement, the catheter slides upward and downward along the posterior tracheal wall. Without the angled distal end, the catheter tip would be allowed to drag against the posterior tracheal wall, mucous would be scooped into the tip and occlusion would be more likely to occur.

Additionally, the angled distal end of the catheter of the present invention reduces irritation of the posterior tracheal wall arising from contact with the tip of the catheter, and also deflects gas and irrigant flow away from said wall.

One presently preferred method for manufacturing the transtracheal catheter of the present invention is by a coextrusion process. Two materials are coextruded to form a double walled catheter. The outer layer or wall is formed of a material which is hydrophobic, and not attractive to mucous. This material generally has a low coefficient of friction so that the mucous easily slides off. An example of an appropriate material is a polyamide-type material.

The inner layer or wall is formed of a more flexible material, such as urethane, that is resistant to kinking. This material, although it may be attractive to mucous, is protected from the mucous by the outer wall. The inner layer or wall is generally much thicker than the outer layer or wall so that the overall transtracheal catheter will be sufficiently resilient and supple to resist kinking, yet the outer wall will be sufficiently rigid and thick to provide sufficient rigidity so that the catheter will not move excessively in the event of abrupt or rapid inhalation or exhalation. The outer layer of material, chosen for its resistance to mucous and added rigidity, can be relatively thin. At the proximal end of the catheter a hub assembly is connected for attachment to oxygen and irrigation devices.

Although coextrusion has been found to be a successful method of forming the transtracheal catheter of the present invention, other methods can also be used. One method could be by dip coating a mucous resistant material over an inner wall formed of a material that is softer and more flexible.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered limiting of its scope, the invention and the presently understood best mode for making and using the invention will be described and explained with additional specificity and detail through the use of the accompanying drawings in which.

In the drawing figures, like parts have been designated with like numerals throughout.

DETAILED DESCRIPTION OF THE PREFERRED EMBODIMENT

Figure 1:
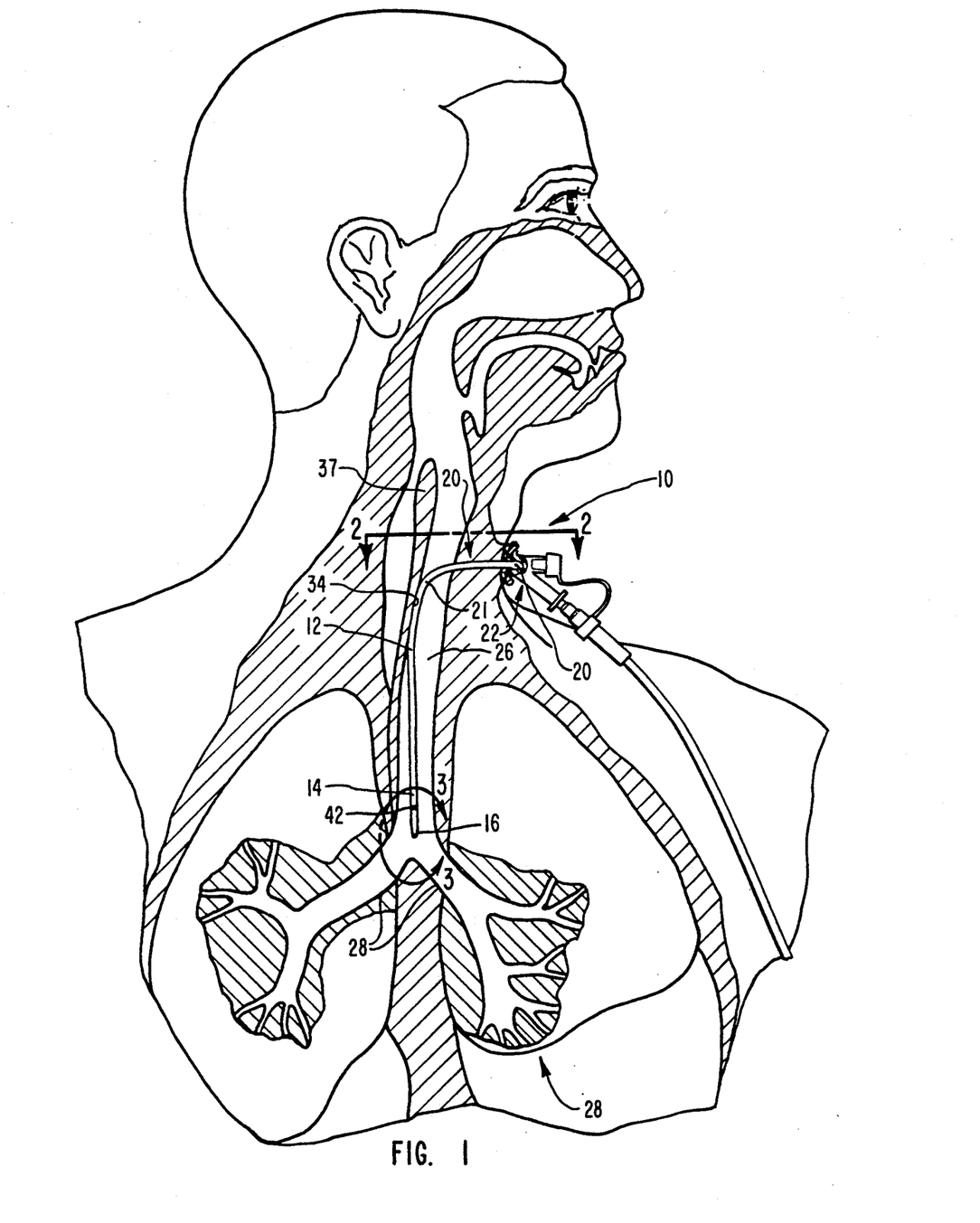
FIG. 1 is a perspective view of one presently preferred embodiment of the present invention illustrating the insertion of the transtracheal catheter into the trachea of a patient.
Figure 6:
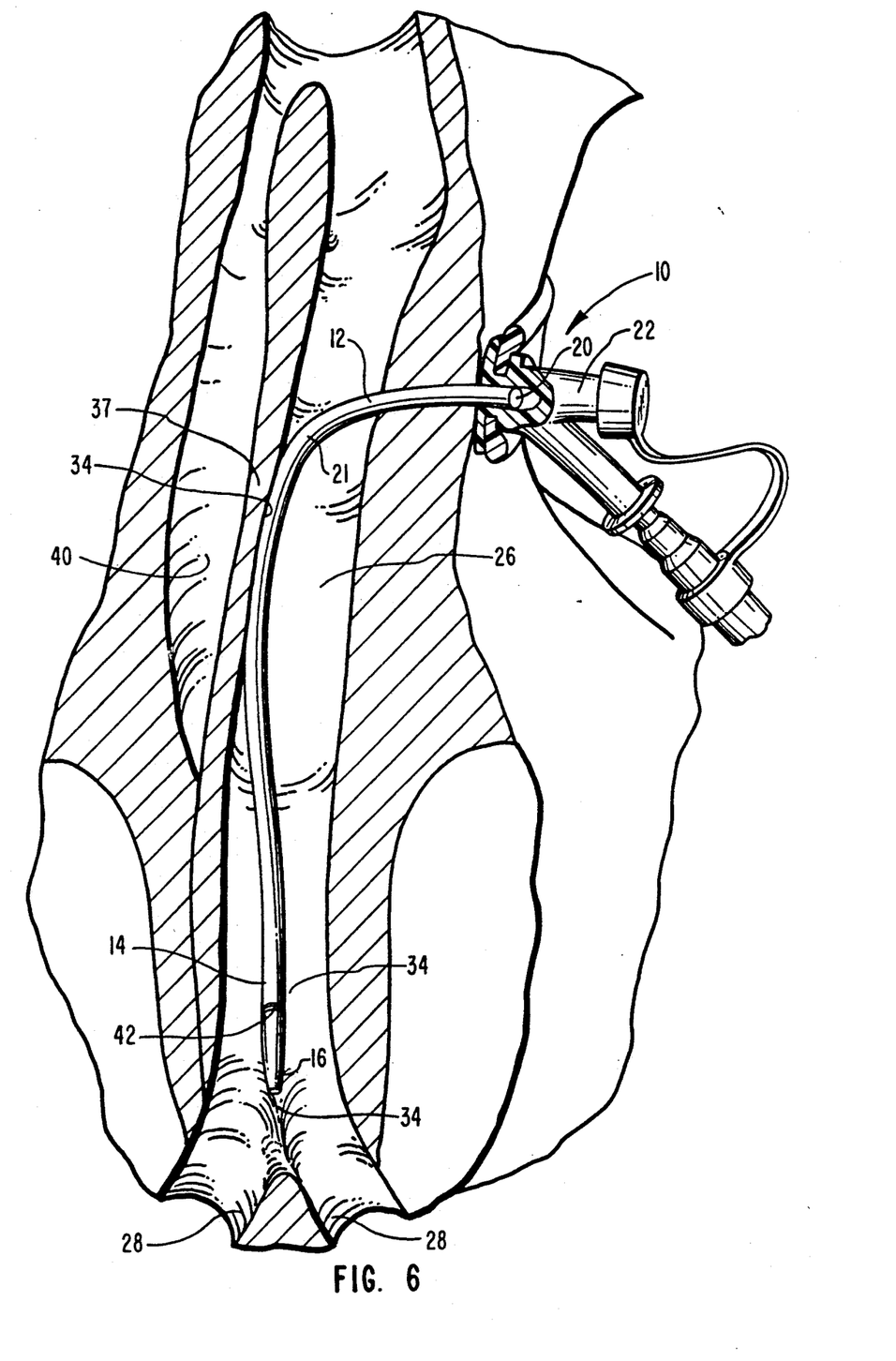
FIG. 6 is an enlarged perspective view with portions broken away particularly illustrating placement of the transtracheal catheter in a patient's trachea, and which illustrates how the transtracheal catheter is firmly held in place against the posterior wall of the trachea with the distal end angled away from the posterior wall.

Reference is first made to FIGS. 1 and 6 which illustrate the use of the present invention. The transtracheal catheter apparatus is generally designated at 10 and is comprised of an elongated catheter body 12 which terminates at its distal end 14 in a smoothly tapered tip 16, and which is attached at its proximal end 20 to a Y connector 22. Distal end 14 of the elongated catheter body 12 is smoothly tapered at tip 16, so as to minimize the possibility of damage to the trachea 26.

The catheter 10 is inserted into the trachea 26 through a small puncture made at the base of the patient's neck. Insertion at this position allows oxygen to be delivered directly into the trachea 26, ensuring that less or no oxygen is lost or wasted. Once the catheter 10 is inserted into the trachea 26, it bends at point 21 sharply downward, making an essentially 90° bend and being positioned such that it rests along the posterior wall 34 of the trachea. As illustrated best in FIG. 6, preferably the catheter body 12 will be firmly held against the posterior tracheal wall 34 from the point of bend 21 to the distal tip 16.

Figure 3:
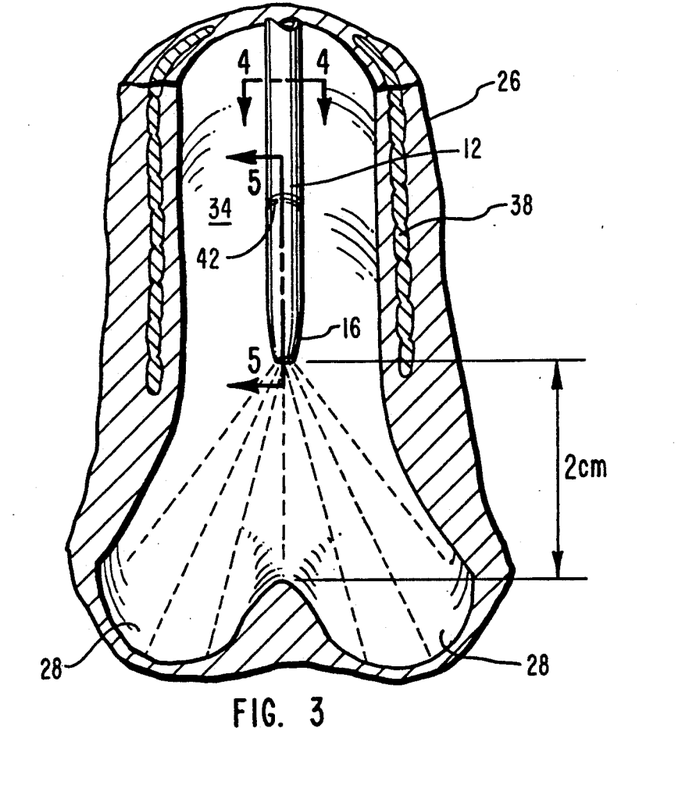
FIG. 3 is a cross-section taken along the line 3—3 of FIG. 1 and illustrating the placement of the catheter such that fluids emanating from the bent distal tip of the catheter evenly and directly reaches the right and left lung.

As can be seen best from FIGS. 1, 3 and 6 taken together, the catheter 10 is long enough so that when it is inserted into the trachea 26 the tapered tip 16 will be positioned about two centimeters from the point where the left and right main stem bronchi 28 begin. As will be further described below, double wall construction of the elongated catheter body 12 is designed so that it has characteristics of stiffness, resiliency, suppleness and circular memory such that the elongated catheter body 12 will be gently curved as illustrated at the point 21 without kinking during use, and is yet stiff enough so that unwanted movement during rapid or abrupt inhalation or exhalation will be minimized in order to reduce or minimize irritation to the trachea.

Figure 2:
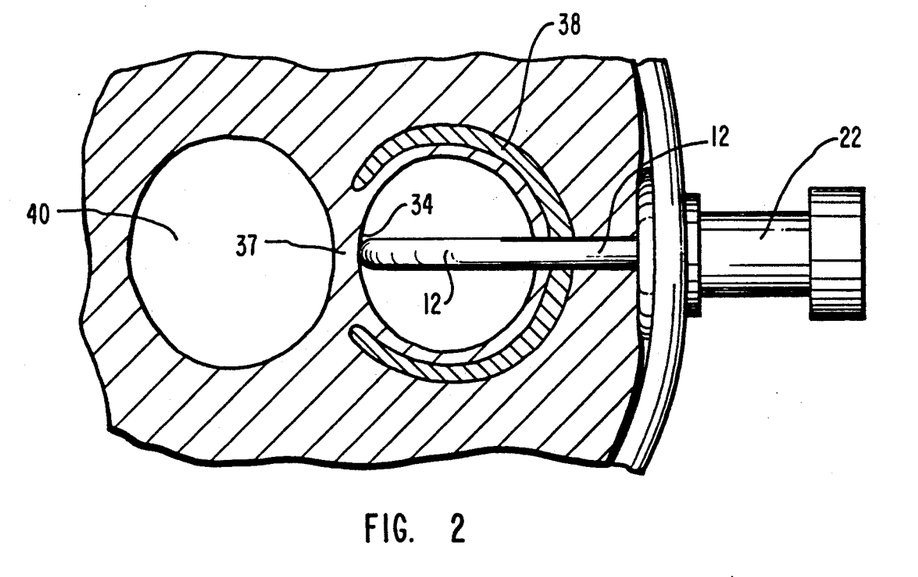
FIG. 2 is a cross-section taken along the line 2—2 of FIG. 1, illustrating the placement of the catheter against the soft membranous back wall of the trachea.

The posterior wall 34 of the trachea 26 is made of soft membranous tissue. Around the sides and front of the trachea 26 are rigid rings 38 (see FIGS. 2 and 3). If a transtracheal catheter is positioned over these rigid rings 38, the catheter tends to cause irritation to the trachea However, at the posterior wall 34 of the trachea 26, there are no rings, only the soft membranous tissue. When the catheter 10 of the present invention is placed within the trachea 26, it is thus preferably centered over the posterior wall 34. Because, as described further below, an outer wall 58 (see FIGS. 4 and 5) adds a degree of stiffness to the elongated catheter body 12, the catheter body 12 will tend to rest and be firmly held against posterior wall 34. The advantage of holding the catheter body 12 firmly against this wall 34 is that there is less sensation of movement since the posterior wall 34 is smooth, not ringed, resulting in less irritation and coughing. FIGS. 2 and 6 illustrate the positioning of catheter body 12 against the posterior wall 34. As can be seen, the catheter 12 does not puncture the wall 37 between the trachea and the esophagus 40 but instead remains within the trachea 26, and follows the posterior wall 34 down to a point near the left and right main stem bronchi 28 (FIGS. 1, 3 and 6).

Referring now to FIG. 3, it can be seen that the catheter 10 is positioned so that the tapered tip 16 terminates about two centimeters from the area of branching of the right and left main stem bronchi 28. At this position, oxygen, saline medication or such fluids as are injected through the catheter 10 will tend to be sprayed evenly between the right and left lung.

Figure 5:
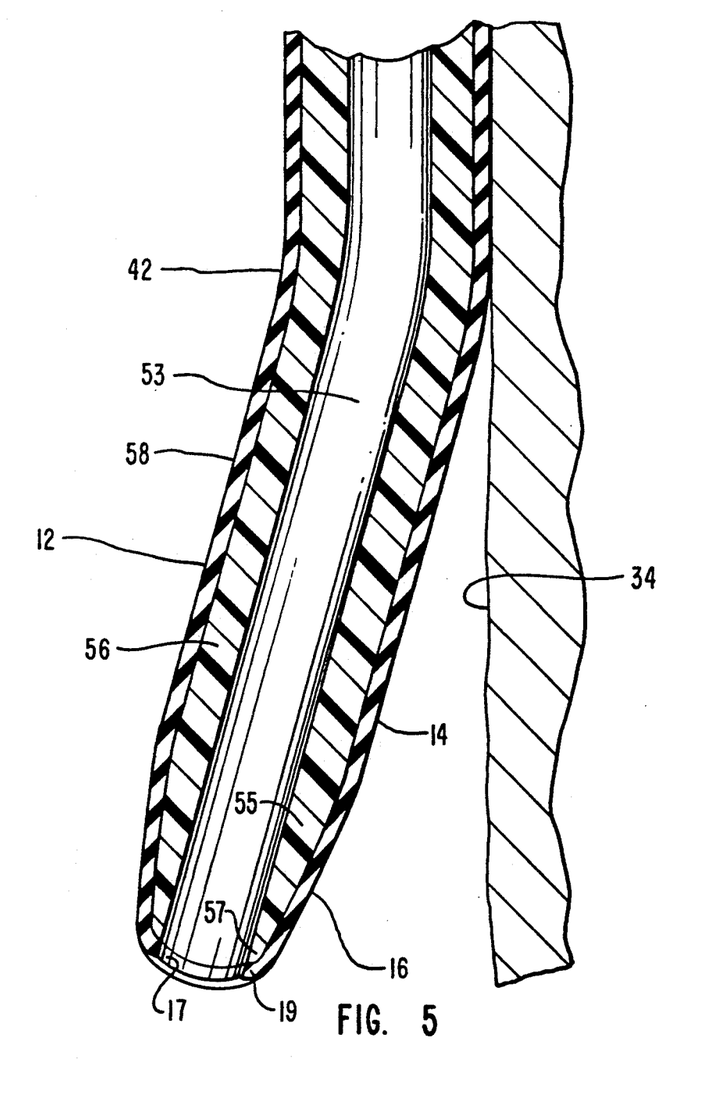
FIG. 5 is a cross section view taken along line 5—5 of FIG. 3, illustrating the inner and outer layers of the transtracheal catheter of the present invention, and its smoothly tapered tip and angled distal end.

In the preferred embodiment within the scope of the present invention, the distal end 14 of catheter body 12 is bent at an angle 42 away from the remaining portion of the catheter 10. When the catheter body 12 is inserted into the trachea, this angle 42 of distal end 14 allows distal end 14 to be deflected away from posterior wall 34 such that distal end 14 is not in contact with posterior wall 34. A cross-section of distal end 14 deflected away from posterior wall 34 is best illustrated by FIG. 5.

Several advantages arise from distal end 14 being bent into angle 42. Initially, when distal end 14 is bent at an angle 42 away from the remaining portion of catheter body 10, movement of the catheter upward and downward along the trachea 26 without causing excessive mucous buildup on its tip 16 is made possible. This can be an important feature as catheter body movement may naturally occur whenever the user breathes, swallows, coughs or moves his or her head.

When a straight catheter is positioned along the posterior wall of the trachea, the tip of the catheter may contact and drag against the posterior wall during catheter movement. This contact in effect scoops mucous from the posterior wall onto the tip of the catheter and into the lumen. Such action may lead to mucous buildup on the tip of the catheter which may in turn cause blockage of the catheter opening.

In contrast, when the distal end 14 of the catheter body 12 is angled, the tip 16 on the distal end 14 projects away from the posterior wall 34 of trachea 26. There is consequently no contact between the tip and the posterior wall 34 of the trachea 26. Mucous is thus not actively scooped onto and into the tip 16 of the catheter body 12.

Another advantage to having the distal end 14 at an angle 42 is the resulting reduction in the amount of irritation caused to the posterior wall 34 of the trachea 26. Generally, when two layers of material come together at a meeting point, that meeting point becomes a natural abrasive area. This situation is present at the tip 16 of the catheter body 12, where the ends of the inner layer of material and outer layer of material join. The natural abrasive area that results may then cause some irritation to any tissue with which it comes into contact. In the present invention, the angle 42 of the distal end 14 prevents contact between the tip 16 and the posterior wall 34, and so assists in preventing this irritation. As the tip 16 of the distal end 14 is angled away from the posterior wall 34 of the trachea, the tip 16 with its natural abrasive point does not constantly rub against and irritate the trachea walls.

A second way in which the angle 42 in distal end 14 assists in reducing irritation to posterior wall 34 of the trachea 26 is by directing the spray of material introduced through the catheter away from the posterior wall 34. The angle 42 allows the material to be projected outward into the lumen of the trachea rather than downward against the posterior wall of the trachea where otherwise two things occur: firstly, irritation to the posterior wall; and secondly, inefficient use of the material.

With a straight catheter, although correct positioning of the catheter tip would allow the spray to be evenly spread between the right and left main stem bronchi as desired, the material is initially sprayed downward, against the posterior wall of the trachea. When the material is a gas, the downward spray against the posterior wall of the trachea causes irritation to the mucosa. The gas dries the mucosa, thereby causing a tickle sensation which in turn causes coughing in the user. When the material is an irrigant, the downward spray against the posterior wall results in an inefficient use of the material. When the material first contacts the posterior wall, part of the material remains on the posterior wall as large droplets rather than going into the right and left bronchi of the lungs, as desired. In the present invention, however, the distal end 14 is angled away from the posterior wall of the trachea. Therefore, the material is projected outward and directly into the main stem bronchi. FIG. 3 illustrates the outward spray of material from the distal end 14 with angle 42 into the right and left bronchi and away from posterior wall 34.

Figure 4:
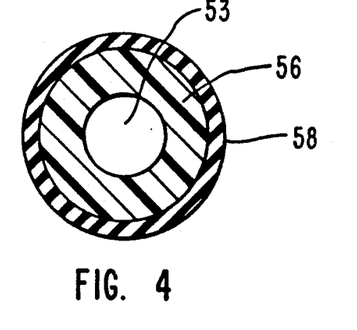
FIG. 4 is a cross-section taken along line 4—4 of FIG. 3, illustrating the double wall or multi-layered construction of the present invention.

Referring now to the cross-sections of FIGS. 4 and 5, it can be seen that catheter body 12 is comprised of an inner wall or layer 56 and an outer wall or layer 58. Each wall or layer is comprised of a material which has specifically selected characteristics and each is designed with a relative thickness to achieve desired overall characteristics as described below.

Inner wall or layer 56 comprises, for example, a material which is soft and flexible enough so that it will bend, but not kink during prolonged use. The outer wall or layer 58 comprises a material that is hydrophobic and has a low coefficient of friction such that the mucous within the trachea does not adhere to the outer wall 58 and cause blockage of the opening 17 or trachea 26. The material of the outer layer 58 must be resistant to moisture and have a low coefficient of friction so that when mucous contacts the outer layer 58, it readily slides down the outer layer 58 and off the catheter 10.

The outer wall or layer 58 thus protects the catheter 10 against mucous buildup. As long as outer layer 58 covers all exposed areas of the catheter body 12, mucous buildup will be prevented. Accordingly, as shown best in FIG. 5, outer wall or layer 58 curves around and fully covers as shown at 19 the extreme end 57 of inner wall or layer 56, thus insuring that the inner layer 56 is completely isolated from mucous. Since oxygen is typically being injected essentially constantly through the catheter 10, mucous cannot migrate into the inner lumen 53 defined by the inner wall 56. Further, it is to be noted that inner wall or layer 56 tapers at 55 to form the gently tapered tip portion 16.

The outer layer 58 need not be very thick. In one preferred embodiment within the scope of the invention, the outer layer 58 is one-fourth the thickness of the inner layer 56. Generally, the outer layer 58 need only be thick enough to cover the catheter body 12 to protect it from the mucous so that the catheter may stay in the trachea for a longer period of time without having to be often removed for cleaning, and/or to provide the desired degree of stiffness to prevent or minimize unwanted movement. Thus, outer layer 58 need only serve as essentially an exoskeletal member of the catheter body 12.

The inner layer 56 is preferably of a greater thickness. The purpose of this layer is to provide flexibility to the catheter so that it can bend yet not kink when placed in the trachea for long periods of time. The thickness of this inner layer 56 also provides the support for the catheter. Since the inner wall or layer 56 is entirely enclosed within the protective outer layer 58, it need not be hydrophobic and mucous resistant. It must only be soft, flexible, with good characteristics of resiliency and circular memory so as to be kink resistant. The respective widths of inner layer 56 and outer layer 58 can best be seen in FIGS. 4 and 5. In one presently preferred embodiment the outer wall is, for example, 0.003 inches in thickness, and is comprised of polyester block amide (PEBAX TM), and the inner wall is 0.012 inches in thickness, and is comprised of urethane. Other possible materials from which outer wall 58 could be formed comprise polytetrafluoroethylene or polyethylene, or other polyamide-like materials. Other possible materials from which inner wall 56 could be formed include natural rubber or other flexible polymer or latex-type materials.

The inner and outer layers 56 and 58 smoothly taper to the tip 16 at the distal end 14 of catheter 12. The tip 16 is smoothly tapered so that the catheter will not tend to damage the body tissues of the trachea 26. (However, as stated earlier, the meeting place of the inner and outer layers 56 and 58 will still be somewhat of a natural abrasive area and will still be somewhat irritable to the tissues.) The tip 16 is also tapered gradually so that spray exiting from the catheter 10 is spread equally between the right and left lung. Again, as noted above, the outer layer 58 completely wraps around and covers the inner layer 56 as shown at 19 in FIG. 5 as a protection against mucous contact.

One method of manufacturing the catheter of the present invention is by co-extrusion processes such as are known in the art. An advantage of using this process is that the overall catheter diameter can easily be made smaller or larger as dictated by the needs of particular patients.

Another possible method of manufacturing the catheter of the present invention is by dipcoating catheters formed of flexible kink resistant material using material that is hydrophobic and resistant to the adherence of mucous. With this dipcoating method, the outer material need not be a material that is extrudable. For example, polytetrafluoroethylene, a hydrophobic but not easily co-extrudable material, may be used in this way.

From the foregoing, it will be appreciated that a substantial advantage of the catheter apparatus of the present invention is that because of the materials of which the catheter body is comprised, and the specific characteristics of the materials of the outer and inner walls, the catheter can be left within the body for longer periods of time without kinking and/or mucous buildup. The catheter of the present invention also permits positioning within the trachea so that there is minimal unwanted movement and hence irritation of the trachea. An additional advantage of the catheter of the present invention is that it allows positioning such that the fluid being injected from the catheter is dispersed evenly between the right and left lung and outward away from the posterior wall of the trachea.

It will also be appreciated that with the catheter of the present invention, irritation to the posterior wall of the trachea by contact with the tip of the catheter is reduced. Additionally, mucous buildup occurring during movement of the catheter along the posterior wall of the trachea in response to breathing, swallowing, coughing, etc., is reduced.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description, and all changes which come within the meaning and range of equivalency of the claims are to be embraced within their scope.

What is claimed and desired to be secured by United States Letters Patents is:

1. A transtracheal catheter comprising:
   an elongated catheter body comprising:
     an inner layer and means to resist kinking of said inner layer and including constructing said inner layer of a material that is soft and flexible to the extent that it will bend rather than kink when placed within a patient's trachea for extended periods of time; and
     an outer layer fused to the inner layer and comprising a material that is sufficiently hydrophobic and that has a sufficiently low coefficient of friction such that said outer layer is resistant to mucous buildup when placed in the trachea, said outer layer essentially completely covering said inner layer to prevent contact of mucous by the inner layer, and in combination with said inner layer provides said catheter body with enough softness and flexibility to bend rather than kink when placed within a patient's trachea for an extended period of time, and with enough rigidity to hold said catheter body firmly against a posterior wall of the trachea to minimize unwanted movement of the catheter body;
   a proximal end and a distal end, said distal end being bent away from said catheter body at an angle such that when said catheter body is inserted into the patient's trachea and placed against the posterior wall of the trachea, said distal end is correspondingly deflected at said angle from the posterior wall; and
   means for connecting said catheter body to an oxygen source said means for connecting being located at said proximal end of said catheter body.

2. A transtracheal catheter as defined in claim 1, wherein said distal end is bent away from said catheter at an angle of 15°.

3. A transtracheal catheter comprising:
   an elongated catheter body defining an inner lumen therethrough and comprising:
     an inner wall and means to resist kinking of said inner wall and including constructing said inner wall of a material that is soft and flexible to the extent that it will bend rather than kink when placed within a patient's trachea for extended periods of time, and said inner wall having a first cross-sectional thickness, and
     an outer wall fused to the inner wall and comprising a material that is more rigid and less flexible than the material of said inner wall, said outer wall having a cross-sectional thickness which is less than the cross-sectional thickness of said inner wall but which, in combination therewith, provides said catheter body with enough softness and flexibility to bend rather than kink when placed within a patient's trachea for an extended period of time, and with enough rigidity to hold said catheter body firmly against a posterior wall of the trachea to minimize unwanted movement of the catheter body;
   a proximal end and a distal end, said distal end being bent away from said catheter body at an angle such that when said catheter body is held firmly against the posterior wall of the trachea, said distal end is correspondingly deflected at said angle from the posterior wall; and
   means for connecting said catheter body to an oxygen source.

4. A transtracheal catheter as defined in claim 3, wherein said distal end is bent away from said catheter body at an angle of 15°.

5. A transtracheal catheter comprising:
   an elongated catheter body defining an inner lumen therethrough and comprising:
     an inner wall and means to resist kinking of said inner wall and including constructing said inner wall of a material that is soft and flexible to the extent that it will bend rather than kink when placed within a patient's trachea for extended periods of time, and said inner wall having a first cross-sectional thickness; and
     an outer wall fused to the inner wall and comprising a material that is more rigid and less flexible than the material of said inner wall, said outer wall having a cross-sectional thickness which is less than the cross-sectional thickness of said inner wall but which, in combination therewith, provides said catheter body with enough softness and flexibility to bend rather than kink when placed within a patient's trachea for an extended period of time, and with enough rigidity to firmly hold said catheter body against a posterior wall of the trachea to minimize unwanted movement of the catheter body, and wherein said outer wall is also sufficiently hydrophobic and has a low enough coefficient of friction so that said outer wall is resistant to mucous buildup, and wherein said inner wall terminates at a point within said inner lumen and said outer wall wraps around said inner wall at said point so as to essentially completely cover said inner wall to prevent contact of mucous by the inner wall;
   a proximal end and a distal end, said distal end being bent away from said catheter body at a 15 degree angle such that when said catheter body is inserted against the posterior wall of the trachea, said distal end is deflected away from the posterior wall at a 15 degree angle thereby reducing irritation to the posterior wall by said distal end of said catheter body rubbing against the posterior wall, and reducing occlusion of said distal end by mucous obtained from the posterior wall; and
   means for connecting said catheter body to an oxygen source, said means for connecting being attached to said proximal end of said catheter body, 6. A transtracheal catheter comprising:

an elongated, flexible catheter body having a length sufficient to permit insertion into a patient's trachea to a point near the patient's left and right main stem bronchi, said catheter body comprising:

an inner wall and means to resist kinking of said inner wall and including constructing said inner wall of a material that is soft and flexible to the extent that it will bend rather than kink when placed within a patient's trachea for extended periods of time, and said inner wall having a first cross-sectional thickness; and an outer wall fused to the inner wall and comprising a material that is more rigid and less flexible than the material of said inner wall, said outer wall having a cross-sectional thickness which is less than the cross-sectional thickness of said inner wall but which, in combination therewith, provides said catheter body with enough softness and flexibility to bend rather than kink when placed within a patient's trachea for an extended period of time, and with enough rigidity to hold said catheter body firmly against a posterior wall of the trachea to minimize unwanted movement of the catheter body;

a proximal end, said proximal end being attached to a means for connecting said catheter body to an oxygen source; and a distal end, said distal end being bent at an angle such that when said catheter body has been fully inserted into the patient's trachea, said distal end will terminate near the left and right main stem bronchi but will also be bent away from the posterior wall of the trachea such that said distal end does not contact the posterior wall although substantially the rest of the catheter body will be in contact with the posterior wall, thereby reducing irritation to the posterior wall at said distal end and reducing possibility of occlusion of said distal end by mucous buildup which may occur during any catheter movement.

7. A transtracheal catheter as defined in claim 6, wherein said distal end is bent away from said catheter body at an angle of 15 degrees.

* * * * *

UNITED STATES PATENT AND TRADEMARK OFFICE
CERTIFICATE OF CORRECTION

PATENT NO. : 5,199,427
DATED : April 6, 1993
INVENTOR(S) : RICHARD D. STRICKLAND It is certified that error appears in the above-identified patent and that said Letters Patent is hereby corrected as shown below:

```
Title page, column 1, line 4, "CAATHETER" should be --CATHETER--
Column 1, line 3, "CAATHETER" should be --CATHETER--
Column 2, line 9, "there is" should be --there are--
Column 2, line 27, "desireable" should be --desirable--
Column 5, line 61, after "trachea" insert --.--
Column 9, line 52, after "source" insert --,--
Column 10, line 67, "body," should be --body.--
```

Signed and Sealed this

Twenty-fifth Day of January, 1994

Attest:

BRUCE LEHMAN

Attesting Officer    Commissioner of Patents and Trademarks